(12) United States Patent
Lee et al.

(10) Patent No.: US 8,906,488 B2
(45) Date of Patent: Dec. 9, 2014

(54) BIODEGRADABLE BLENDS AND FILMS HAVING NANO-STRUCTURAL FEATURES

(75) Inventors: JaeHong Lee, Yongin-si (KR); James H. Wang, Appleton, WI (US); Gregory Wideman, Menasha, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 521 days.

(21) Appl. No.: 12/836,374

(22) Filed: Jul. 14, 2010

(65) Prior Publication Data
US 2012/0015142 A1 Jan. 19, 2012

(51) Int. Cl.
| | |
|---|---|
| *C08L 1/08* | (2006.01) |
| *C08L 1/02* | (2006.01) |
| *A61F 13/511* | (2006.01) |
| *A61F 13/514* | (2006.01) |
| *C08J 5/18* | (2006.01) |
| *C08L 1/14* | (2006.01) |
| *C08L 69/00* | (2006.01) |
| *C08L 1/10* | (2006.01) |
| *C08L 1/26* | (2006.01) |
| *C08L 1/32* | (2006.01) |
| *C08L 67/04* | (2006.01) |

(52) U.S. Cl.
CPC ............... *C08L 1/02* (2013.01); *A61F 13/511* (2013.01); *A61F 13/514* (2013.01); *C08J 5/18* (2013.01); *C08L 1/14* (2013.01); *C08L 69/00* (2013.01); *C08L 1/10* (2013.01); *C08L 1/26* (2013.01); *C08L 1/32* (2013.01); *C08J 2301/02* (2013.01); *C08J 2301/14* (2013.01); *C08J 2369/00* (2013.01); *C08L 67/04* (2013.01)
USPC ............................................. 428/141

(58) Field of Classification Search
USPC ............................................. 428/141
See application file for complete search history.

(56) References Cited

U.S. PATENT DOCUMENTS

| | | | |
|---|---|---|---|
| 6,573,340 B1 * | 6/2003 | Khemani et al. | 525/437 |
| 6,576,694 B1 | 6/2003 | Liu et al. | |
| 7,357,793 B2 | 4/2008 | Pacetti | |
| 2003/0013821 A1 | 1/2003 | Tan et al. | |
| 2007/0117908 A1 | 5/2007 | Zhou et al. | |
| 2008/0311813 A1 | 12/2008 | Ting et al. | |

FOREIGN PATENT DOCUMENTS

| | | |
|---|---|---|
| EP | 1 857 269 A1 | 11/2007 |
| JP | 2001-348019 A | 12/2001 |
| WO | WO 9608535 A1 | 3/1996 |
| WO | WO 0216468 A1 | 2/2002 |
| WO | WO 2007125039 A1 * | 11/2007 |

OTHER PUBLICATIONS

Supplementary European Search Report dated Nov. 20, 2013, 7 ; pages.

* cited by examiner

*Primary Examiner* — Maria Veronica Ewald
*Assistant Examiner* — Nancy Johnson
(74) *Attorney, Agent, or Firm* — Dority & Manning, P.A.

(57) ABSTRACT

A thermoplastic polymer composition with a tertiary blend of a carbon dioxide-derived polymer, a thermoplastic cellulose derivative, and a thermoplastic compatibilizer is described. The composition can be melt-processed into flexible, thin films that have fine nano-scale structural features in both the cross-directional and machine-directional orientations, for use in various products. The films, which are made from relatively brittle materials, exhibit a greater degree of ductility, elongation capacity, and strength than the primary, original component materials as binary-blends from which the film is made.

12 Claims, 4 Drawing Sheets

BIODEGRADABLE BLENDS AND FILMS HAVING NANO-STRUCTURAL FEATURES

FIELD OF INVENTION

The present invention pertains to a biodegradable polymer composition of matter that is not derived from food-based resources. In particular, the invention relates to a tertiary blend of a carbon dioxide-derived polymer, thermoplastic cellulose derivatives, and a thermoplastic compatibilizer, which can be melt-processed into flexible films.

BACKGROUND

Developing products based on environmental friendly and sustainable materials is becoming an essential in today's marketplace because of increased awareness of environmental impact and depletion of fossil-based petrochemical resources. One approach to provide for environmentally sustainable thermoplastic film materials has been to develop alternative formulations that can incorporate more non-food based biodegradable or renewable materials into the films. For example, thermoplastic films can be fabricated with thermoplastic cellulosic materials that exhibit balanced mechanical properties to address the depletion of petroleum-based resources and the escalation or fluctuation of crude oil prices. Conventional films that are made from thermoplastic cellulose materials have exhibited relatively poor performance qualities. They tend to have low flexibility and a narrow temperature window for thermoplastic processing, which results in a limited range of applications in which the films can be used. For instance, a problem to be solved is the need to develop a thermoplastic film composition that has enhanced flexibility.

SUMMARY OF THE INVENTION

The present invention describes, in part, a thermoplastic material composition having a tertiary blend of about 1 wt. % to about 95 wt. % of a polyalkylene-carbonate (PAC) and about 95 wt. % to about 1 wt. % of a thermoplastic cellulose (TPC) derivative; and about 1 wt. % to about 20 wt. % of a polyhydroxylalkanoate (PHA) compatibilizer. The resulting thermoplastic material exhibits a greater degree of ductility and strength that is greater than a binary blend of polyalkylene carbonate (PAC) with only one of either of the thermoplastic cellulose (TPC) derivative or the polyhydroxylalkanoate (PHA) compatibilizer, individually or alone. In other words, the tertiary blend (PAC+TPC+PHA) can yield better physical properties and than either of the binary blends (PAC+TPC, or PAC+PHA) by themselves when added singularly to PAC.

The composition can be melt-processed into thin films. Ordinarily, a polyalkylene-carbonate and thermoplastic cellulose-based blend exhibits low ductility and low toughness. The present invention, however, by incorporating a small amount of a compatibilizer, the blended film demonstrated significant increase in ductility and reduced modulus, as evidenced by tensile strength testing results of the film material. The inventive film utilizes two non-food based biodegradable polymers as components of the films, enabling one to fabricate films with environmental sustainability benefits. An unexpected result of the present composition is that the combination of separate individual materials with relatively low ductility can generate a more flexible material than the original materials. It is believed that the PAC and cellulose materials in the presence of a compatibilizer formed a better or finer dispersion of the dispersed polymer phase (i.e., either PAC phase or thermoplastic cellulose) into a nano-scale dispersed structural morphology.

In general, according to the present invention, the thermoplastic material composition has a majority component blend of: a) about 1 wt. % to about 95 wt. % of a polyalkylene carbonate and b) about 95 wt. % to about 1 wt. % of a thermoplastic cellulose derivative; and about 1 wt. % to about 20 wt. % of a polyhydroxylalkanate (PHA) compatibilizer. The polyalkylene carbonate is present in an amount from about 10-90 wt. %, and said thermoplastic cellulose derivative is present in an amount from about 90-10 wt. %. The polyalkylene carbonate can be a catalyzed copolymerization product of $CO_2$ and an alkylene oxide. In certain embodiments, the polyalkylene carbonate can be a polypropylene carbonate, polyethylene carbonate, polybutylene carbonate, etc. The thermoplastic cellulose derivative can be a cellulose ester, cellulose ether, or cellulose alkanoate or carboxyl-alkyl cellulose. The cellulose alkanoate possesses two or more different alkanoate groups. In certain embodiments, the cellulose alkanoate is a cellulose acetate butyrate. The polyhydroylalkanoate (PHA) compatibilizer is: poly(3-hydroxy-butyrate)(PHB), poly(3-hydroxy-butyrate-co-3-hydroxy-valerate)(PHBV), poly(3-hydroxy-butyrate-co-4-hydroxy-butyrate), poly(3-hydroxy-butyrate-co-3-hydroxy-hexonate), poly(3-hydroxy-butyrate-co-3-hydroxy-octanoate), and homologues of PHA copolymers and terpolymers, or combination thereof. The composition, when formed into a material body, exhibits ribbon-like nanostructure features composed of a minority phase material evenly dispersed in a majority phase of either said polyalkylene carbonate or said thermoplastic cellulose derivative, whichever of the two is present as a minority species in the continuous phase of majority component in the blend.

Alternatively, present invention relates to an absorbent article or health care product that incorporates a film formed from the tertiary component blend. The film can be part of an inner baffle or an outer cover of the absorbent article, which can be a personal hygiene product, a feminine care product, a diaper, a training pant, or an adult incontinence product. In another embodiment, the film can be used as a packaging film.

In other aspect, the invention relates a method of making flexible film. The method involves providing a tertiary blend of about 1 wt. % to about 95 wt. % of a polyalkylene carbonate and about 95 wt. % to about 1 wt. % of a thermoplastic cellulose derivative, and about 1 wt. % to about 20 wt. % of a polyhydroxyalkanoate (PHA) compatibilizer; melt-blending said tertiary blend, extruding a film, and generating nanostructure features that are evenly distributed throughout said film, which form one of two phases composed of either said polyalkylene carbonate or said thermoplastic cellulose derivative, whichever of the two is present as a minority species in said film. The nanostructure features have an average length dimension from about ¼ or ⅛ to about ¾ or 0.9 of a micrometer when viewing a cross-direction orientation of said film.

Other features and advantages of the present invention will be discussed in the following detailed description and associated figures.

DETAILED DESCRIPTION OF THE INVENTION

The present invention discloses melt-processed tertiary blend compositions and thin films formed from the blends. The compositions include non-food based renewable materials, such as thermoplastic cellulosic materials and environmentally sustainable polymers, and have improved flexible mechanical properties. The blends can be applied potentially in a variety of uses or products, such as packaging films, molding, and component films of consumer products (e.g., personal care and/or health care products), etc. In particular the invention discloses melt-processed tertiary blends comprising a polyalkylene carbonate (PAC) made from carbon dioxide and alkylene oxide, a thermoplastic cellulose (TPC), and a thermoplastic compatibilizer.

A particular kind of polyalkylene carbonate (PAC) is poly(propylene carbonate) (PPC), which is made from the catalyzed copolymerization of carbon-dioxide ($CO_2$) and propylene oxide. PPCs have attracted much attention because of their environmental friendly nature such as utilizing the greenhouse gas waste and biodegradability of PPC polymer. PPCs are amorphous and biodegradable because of the aliphatic polycarbonate ester structure on their backbone. (Li, X. H. et al., *J. Polym. Sci. Part B,* 2004; 4; 666-675.) PPCs with alternating structure can be melt-processed like commercial polyethylene. (Li, X. H. et al., *J. Appl. Polym. Sci.,* 2003; 89; 3301.) PPCs, however, exhibit poor mechanical properties and thermal stability. To improve the plasticity of PPC and evaluate the possibility using it as a plastic that can be easily processed thermally, some blending systems containing PPCs have been studied.

According to the present invention, one can use thermoplastic compatibilizers such as aliphatic polyesters like polyhydroxyalkanoates (PHAs) blends to modify the film plasticity of PPC containing materials. PHAs are linear polyesters produced in nature by bacterial fermentation of sugar or lipids. More than 100 different monomers can be combined within this family to give materials with extremely different properties. Generally, they can be either thermoplastic or elastomeric materials, with melting-points ranging from 40 to 180° C. The most common type of PHAs is PHB (poly-beta-hydroxybutyrate). PHB has properties similar to those of polypropylene, however it is stiffer and more brittle. Poly(3-hydroxybutyrate) (PHB) is a type of naturally occurring thermoplastic polymers currently produced microbially inside of the cell wall of a number of wild bacteria species or genetically modified bacteria or yeasts, etc. It is biodegradable and does not present environmental issues post disposal, i.e., articles made from PHB can be composted. However, it is a highly crystalline material and is therefore quite brittle, this has limited the wide applications of PHB for flexible articles. Furthermore, PHB also has a narrow thermal processing window between its melt temperature and its thermal decomposition temperature. To overcome the difficult processing issues of PHB, a number of alternative poly-hydroxy-alkanoate (PHA) copolymers have been developed. Such copolymers include copolymers having side chain branches of a various lengths or groups, such as poly(3-hydroxybutyrate-co-3-hydroxyvalerate), poly(3-hydroxybutyrate-co-3-hydroxyhexanoate), poly(3-hydroxybutyrate-co-3-hydroxyoctanoate), etc., and also main chain copolymers such as poly(3-hydroxybutyrate-co-4-hydroxybutyrate). A PHB copolymer called PHBV (polyhydroxybutyrate-valerate) is less stiff and tougher, and can be used as a packaging material.

In a blend of poly(3-hydroxybutyrate) (PHB) and PPC, it has been reported that poly(3-hydroxybutyrate) (PHB) exhibited good miscibility with PPC when the PPC content is less than 30 wt. %, and the brittleness of the resultant material improved with the addition of PPC. (Yang, D. Z. et al, *J. Appl. Polym. Sci.,* 2008; 109; 1635-1642.) The crystallization behavior of PHBV/PPC melt blend have also been investigated. PHBV/PPC (30/70 wt. ratio) melt blend incurs a certain extent of trans-esterification reaction, and the crystallinity and linear growth rate of spherulites of PHBV could decrease by the addition of PPC. (Li. J. et al., *J. Appl. Polym. Sci.* 2004; 92; 2514-2521.) The thermal and mechanical property, brittleness, and cold flow-ability of PPC can be improved by blending with poly(butylenes succinate) (PBS) or polybutylene succinate/adipate) (PBSA) while the respective complete biodegradability can be maintained. (Zhou, Q. et al., U.S. Patent Application Publication No. 2007/0117908.) Other workers have reported that polylactic acid (PLA)/PPC blend system in which PLA and PPC were partially miscible but compatible to some extent owing to similar chemical nature of the blend components. (Ma, X et al., *J. Polym. Sci. Part B,* 2006; 44; 94-101.)

According to the invention, thermally processed tertiary blend compositions are composed of a carbon dioxide-based polymer, such as a polyalkylene carbonate (PAC), and a thermoplastic cellulose derivative such as cellulose ester with a thermoplastic compatibilizer, which is a renewable polymer, such as an aliphatic polyester like PHAs. Cellulose esters (CEs) are a particular kind of thermoplastic starch, which are considered an important sustainable material. As produced from cellulose, a biomass produced annually in the largest quantity on earth, it is indeed the most abundant natural polymer renewably produced each year in nature. It can be processed by conventional melt process by the aid of a plasticizer. The common properties of these cellulose esters are their high stiffness, low ductility, good clarity, and narrow thermal processing window. They also have moderate heat and impact resistance. However, the general rigid and brittle nature of CEs resulted in only limited applications.

In particular embodiments, the composition may include polypropylene carbonate (PPC), a thermoplastic cellulose, e.g., cellulose acetate butyrate (CAB), and an aliphatic polyester thermoplastic compatibilizer, such as poly(3-hydroxyalkanoate) (PHA), a specific example of which is poly(3-hydroxybutyrate) (PHB) or poly(3-hydroxybutyrate-co-3-hydroxyvalerate) (PHBV). The tertiary blend films demonstrate unexpectedly enhanced ductility. It is believed, for instance, that the PHB or PHBV helps to mediate or adjust the mechanical and physical properties of PPC and CAB, by changing the microstructure from an irregular, poorly dispersed macro-structure to a more regular and uniform microstructure of nano-dispersed forms or structures.

The polymer blends may include from about 10% to about 90% by weight of polyalkylene carbonate (PAC); typically between about 15 wt. % to about 85 wt. %, alternatively between about 18 wt. % or 20 wt. % to about 75 wt. % or 80 wt. %, or between about 22-25 wt. % or 30-45 wt % to about 68-77 wt. % or 88-90 wt. %. Examples of polyalkylene carbonate include poly-aliphatic alkylene polycarbonate made from cyclic alkylene oxide and $CO_2$. Examples also can include polyethylene carbonate, polypropylene carbonate (PPC), polybuytylene carbonate, or polyhexene oxide. Examples of cyclic aliphatic carbonate may include polycyclohexene carbonate, polynorbornene carbonate, polylimonene carbonate, etc. One may also include about 10 wt. % to about 90 wt. % of a thermoplastic cellulose; typically between about 15-20 wt. % to about 85-88 wt. %, or between 25-30 wt. % to about 70-78 wt. %. Examples of thermoplastic cellulose include cellulose esters (e.g. cellulose acetate, cellulose propionate, cellulose butyrate, celluose hexanoate, other cellulose alkanoates), celluose ethers (methyl cellulose, ethyl cellulose, hydroxyethyl celluose, hydroxypropyl cellulose, hydroxybutyl cellulose, etc.) and other cellulose derivatives which can be melt processed using a thermoplastic process. The blend composition further includes from about 1% to about 20% by weight of a thermoplastic compatibilizer which is capable of emulsifying and compatibilizing the normally incompatible blend components of TPC and PAC. Typically the compatibilizer is present in a range of about 2 wt. % or 3 wt. % to about 15 wt. % or 17 wt %, or between about 4-5 wt % to about 10-12 wt. %.

Examples of the compatibilizers include aliphatic polyesters such as polyhydroxyalkanotae (PHA), (e.g., poly(3-hydroxybutyrate)(PHB), poly(3-hydroxy-butyrate-co-4-hydroxybutyrate)(3HB4HB), or poly(3-hydroybutyrate-co-3-hydroxyvalerate)(PHBV), poly(3-hydroxybutyrate-co-3-hydroxyhexanoate)(3HB3-BH), poly(3-hydroxybutyrate-co-3-hydroxyoctanoate), etc.

The PPC/CAB binary-blend films and PPC/CAB/PHB or PPC/CAB/PHBV tertiary-blend films were prepared by means of a single-step, direct melt blending-film casting process. Alternatively, polymer blends of PPC, CAB, and PHB or PHBV can be produced by melt extrusion in a thermoplastic processing device such as an extruder, subsequently films such as blown film or cast is fabricated from the polymer blends. PPC/CAB blend film showed low ductility and low toughness, whereas PPC/CAB with the addition of small amount of PHB showed significantly increased ductility and reduced modulus, as evidenced by the tensile testing results of films. This improvement in film ductility and flexibility is believed to be attributed to the microstructural change resulting in better dispersion of the minority phase by the addition of PHB or PHBV as a compatibilizer demonstrated by Scanning Electron Microscopy (SEM). FIGS. 1A and 1B, and 2A and 2B provide SEM photos of binary-blended films formed using CAB and PPC materials at different percentages, showing their respective morphology in each set of Figures (A=MD, B=CD) along CD and MD orientations. In comparison, the morphological changes derived in the tertiary-blended films are represented in FIGS. 3A and 3B, and 4A and 4B, respectively along CD and MD orientations for each set of Figures. One can observe that the corresponding morphologic features shown in the images of FIGS. 1A and 1B, and 3A and 3B, and of FIGS. 2A and 2B, and 4A and 4B, are generally reduced in size by a factor of over 2-3 on average. This general reduction in size of the morphological structures, it is believed helps improve the ductility of the film material. Further detailed discussion of the morphology will be provided below.

The present inventive tertiary blended composition can be formed into a variety of thermoplastic extruded articles, such as fibers, moldings, packaging films, and consumer product component films. According to an embodiment of the present invention, thin thermoplastic films having a thickness from 5 micron to 50 micron made from the tertiary blend compositions still retain similar flexibility and tensile properties as to conventional films that are not of the tertiary blend. An advantage of the present inventive films is that it allows one to employ two non-food based biodegradable polymers as basic components of the films, which provides films that are environmentally more sustainable than conventional petrochemical-based polymers.

Section I.—Physical Properties of Film

When formed into a flexible thermoplastic film, the tertiary blend in its broadest sense has 1) about 1 wt. % to about 95 wt. % of a polyalkylene carbonate and 2) about 95 wt. % to about 1 wt. % of a thermoplastic cellulose derivative, respectively forming a either a major or minor component of said film, and 3) about 1 wt. % to about 20 wt. % of a polyhydroxylalkanoate (PHA) compatibilizer. The film exhibits nanostructural features that are at least $\frac{1}{3}$ to $\frac{1}{10}$ of the size of corresponding structural morphology in a film formed from a binary blend of a precursor thermoplastic material of said polyalkylene carbonate and said thermoplastic cellulose derivative, absent said polyhydroxylalkanoate (PHA) compatibilizer, and the nanostructural features have a ribbon-like nano-morphology, and form one of two phases composed of either the polyalkylene carbonate or the thermoplastic cellulose derivative, whichever one of the two is present as a minority species in the majority component. The film exhibits an islands-in-a-sea type morphology of nanostructure features of polyalkylene carbonate, which are evenly distributed throughout a material body of the film in a matrix of thermoplastic cellulose derivative material, when the polyalkylene carbonate is a minority species. The nanostructure features have an average length dimension from about 0.10 or 0.125 to about half (0.50) or 0.75 or 0.85 of a micrometer (μm).

Surprisingly, the film exhibits an elongation-at-break value that is increased by at least 150% to about 500% of a film formed from a binary blend of a polyalkylene carbonate and a thermoplastic cellulose derivative absent the polyhydroxylalkanoate (PHA) compatibilizer. The film exhibits an elongation-at-break value increase of about 150% to about 700% relative to a film formed from said binary blend when stretched along a machine-direction orientation. Alternatively, the film can exhibit an elongation-at-break value increase of between about 200% to about 500% in a film formed from the binary blend when stretched along a cross-direction orientation.

The film exhibits also unexpected improvement in energy at break, i.e., the relative improvement in toughness of the film. The improvement in energy at break ranges from about 200% up to about 800% (typically, about 250% or 300% to about 470% or 500%) increase for comparable compositions that have a presence of PHA compatibilizer versus those compositions that do not contain polyhydroxylalkanoate (PHA) compatibilizer.

Film Mechanical Properties

The mechanical properties of the blend films, as shown in Tables 1, 2, and 3, were determined on a Sintech 1/D with five samples tested in both the machine direction (MD) and the cross direction (CD). The film samples were cut into pieces with larger terminal lobes at each end, such as "dog-bone" shapes, with a center width of 3.0 mm before testing. The dog-bone film samples were held in place by grips on the Sintech set to a gauge length of 18.0 mm. During the test, samples were stretched at a crosshead speed of 5.0 inches per minute until breakage occurred. The computer program TestWorks 4 collected data during the test and generated a stress (MPa) versus strain (%) curve from which a variety of properties were determined: e.g., modulus, peak stress and elongation.

Peak Stress of Blend Films

As shown in Tables 1, 2, and 3, all film samples have a greater peak stress in the machine direction (MD) than cross direction (CD). Peak stress values for the CAB film (Exp.1: 83 MPa in MD, 33 MPa in CD, respectively) appear to be much higher than that of samples made from pure PPC (Exp.7: 34 MPa in MD, 32 MPa in CD). As PHB is added to the film formulation, the peak stress values of blend films tended to decrease. Addition of 5 wt. % of PHB in CAB/PPC blending system induced a slight decrease of peak stress. Addition of PHBV in CAB/PPC (70/30) formulation also resulted in slight decrease of peak stress, as shown in Table 3. Addition of PHBV in CAB/PPC blend (30/70) with majority of PPC did not appear to change the peak stress of the blend film samples.

Elongation %-at-Break of Blend Film

The tertiary blend enables one to make a more ductile film that exhibits greater ductility as measured by elongation percent (%) at break of between about 2× and about 8× increase over an original film with a binary blend. Additionally, elongation percent-at-break of the tertiary blend film is increased by a range of about 3× to about 7× in terms of stretched linear dimensions over the original dimensions. That is to say, the film can be elongated between about 300% to about 700% of original dimensions in either CD and MD orientation. As summarized in Table 1, the elongation percent-at-break property in machine direction (MD) of the CAP/PPC binary blend films exhibited a dramatic decrease with the addition of CAB as compared to the elongation percent-at-break value in a pure PPC film; however, the CD elongation percent-at-break of CAB/PPC binary blend film in cross direction (CD) only decreased at a CAB/PPC ratio of 10/90 (decrease from 14% to about 3%, while the CD elongation percent-at-break for all other CAB/PPC ratios all increased substantially, ranging from 27% to 38% for the binary blend film versus pure PPC film of only 14%.

In contrast, when tertiary blended films are made at the same CAB/PPC ratio, but adding PHB or PHBV to the CAB/PPC, one observes that the elongation percent-at-break value increases substantially, as shown in Tables 2 and 3. This contrast in phenomenon indicates the likely formation of unfavorable microstructures and poor compatibility between the CAB and PPC polymers in the binary blend films, and formation of favorable or desirable microstructures in the tertiary blend films. The elongation percent-at-break, however, appeared to increase substantially in both the machine direction (MD) and cross direction (CD) when about 5 wt % of PHB is co-blended. The elongation percent-at-break values for CAB/PPC (70/30) increased for MD and CD, respectively, from 26% and 27% to 48% and 60%. In particular, one observes the elongation values for CAB/PPC (30/70) increased significantly, in the MD and CD, respectively, from 20% and 38% to 86% and 183%. This feature represents a surprising 4.3× and 4.8× increase, respectively, which is quite an unexpected result. This result suggests an improvement in the compatibility and formation of desired microstructure with the small amount of added PHB (~5%).

The ductility improvement in the film was also observed in the case of adding PHBV in CAB/PPC film formulation as displayed in Table 3. The elongation values for CAB/PPC (70/30) were increased from 26% and 27% (for MD and CD) to 67% and 100% (5 wt % PHBV addition), 55% and 73% (13 wt % addition), 58% and 34% (17 wt % addition). The elongation for CAB/PPC (30/70) was also increased from 20%, 38% (MD, CD) to 80%, 140% and 89%, 120% by the addition of 5 wt % and 13 wt % of PHBV respectively. Especially 17 wt % of PHBV in CAB/PPC (30/70) showed substantial elongation increase from 20%, 38% (MD, CD) to 110%, 250%, representing a surprising 5.5×, and 6.6 X increase. This suggested the compatibility improvement and formation of desired microstructure as was the same case with the PHB addition.

Energy-at-Break of Blend Film

When looking at the energy-at-break values, the pure PPC film was much tougher than pure CAB film in MD direction. It should be noted that the CD energy-at-break of the pure PPC film is quite low, showing anisotropic properties of the PPC films. It was shown that blending with a small amount of CAB made the PPC/CAB more brittle from the comparison of energy at break value for Experiment 7 (35 J/cm$^3$ in MD, and 2 J/cm$^3$ in CD) and Experiment 6 (9 J/cm$^3$ in MD, and 1 J/cm$^3$ in CD). Similarly with the analysis of peak stress and elongation, this may be due to the poor compatibility between two polymers as discussed previously. By the addition of 5 wt. % PHB, CAB/PPC film became tougher. The Energy-at-break values for CAB/PPC (70/30) film were increased from 12 and 9 J/cm$^3$ (MD, CD) to 22 and 17 J/cm$^3$. Especially the energy-at-break for CAB/PPC (30/70) were increased significantly from 8 and 9 J/cm$^3$ (MD, CD) to 30 and 33 J/cm$^3$ by addition of only 5% PHB.

Similarly with the PHB case, the toughness of CAB/PPC film was increased by the addition of PHBV as shown in Table 3. The Energy-at-break values for CAB/PPC (70/30) film were increased from 12 and 9 J/cm$^3$ (MD, CD) to 27 and 30 J/cm$^3$, 23 and 21 J/cm$^3$, 30 and 20 J/cm$^3$ by the addition of 5, 13 and 17 wt % of PHBV respectively. Especially the elongation for CAB/PPC (30/70) were increased significantly from 8 and 9 J/cm$^3$ (MD, CD) to 30 and 32 J/cm$^3$, 32 and 29 J/cm$^3$, 40 and 54 J/cm$^3$ by addition of only 5% 13 and 17 wt % of PHBV respectively.

Section II.—Microstructure Analysis

The present tertiary blend composition can alter the morphological structure of the drawn film. Selected film samples were examined using a Scanning Electron Microscopy (SEM) to determine whether if there was a correlation between the microstructure of the films and their observed mechanical properties. Cross-sections of film were made to show the structure in both MD as well as in CD orientations. The MD sections were prepared by fracturing the films in the MD direction after first chilling to cryogenic temperature in boiling liquid nitrogen. The CD sections were prepared by cutting the film in the cross-direction using a cryogenically chilled super-Keen razor while the sample was held at cryogenic temperature. The sections were mounted vertically and sputter coated with gold using light burst applications at low current to significantly reduced any possibility of sample heating. All samples were examined in a JEOL 6490LV SEM operated at low voltage. The resulting SEM pictures were shown in FIG. 1A to FIG. 4B.

Microstructures of CAB/PPC Films in the Absence of a Compatibilizer

Figure 1A:
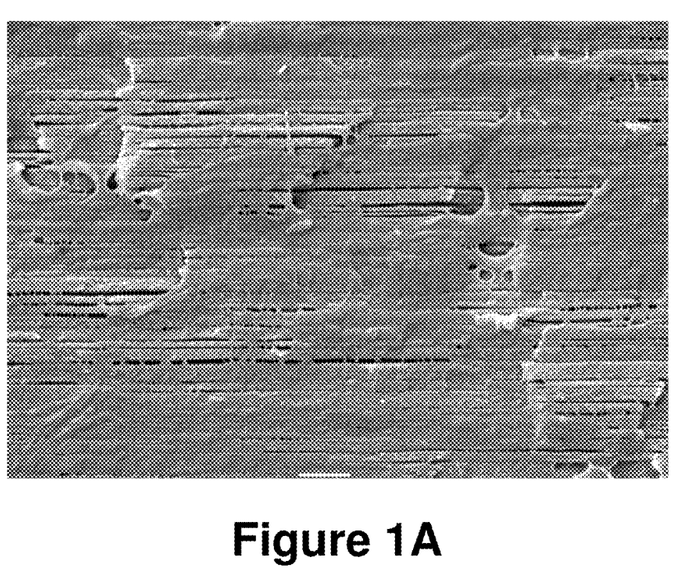
FIG. 1A shows a SEM image of an extruded film material, formed from a binary blend of a thermoplastic cellulose derivative (70%) and a carbon dioxide polymer (30 wt. %), as seen along the MD orientation.
Figure 1B:
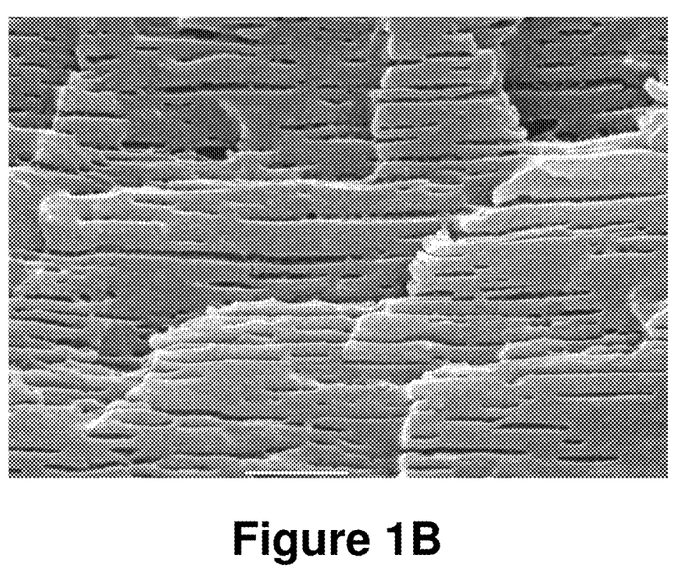
FIG. 1B shows a SEM image of the film of FIG. 1A, as seen in the CD orientation.

Films formed from a binary blend of CAB/PPC (70/30) have striated appearance under scanning electron microscopy (SEM). As shown in FIG. 1A, a binary-blend film of CAB/PPC (70/30) in the MD direction exhibits an overall laminated structure, suggesting that the blend is a heterogeneous layered composite of the two polymers. The CAB laminates of about 100-200 nm thick are oriented in machine direction and have PPC layers of much smaller thickness (~10-70 nanometer sheets), which are formed as an amorphous phase in between the CAB layers. The same films when viewed in cross-direction showed overall brittle fracture mode and laminates, the amorphous PPC phase appears as nano scale bridging material between CAB laminates as displayed in FIG. 1B.

Figure 2A:
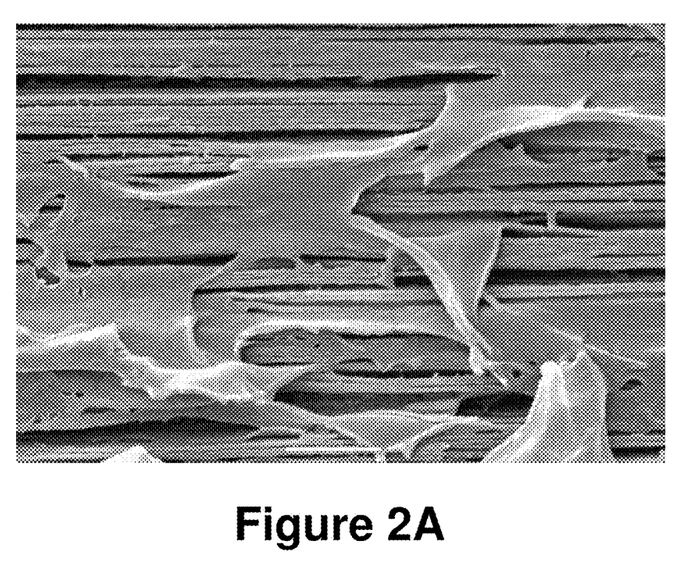
FIG. 2A shows a SEM image of an extruded film material, formed from a binary blend of a thermoplastic cellulose derivative (30 wt. %) and a carbon dioxide polymer (70 wt. %), as seen along the MD orientation.
Figure 2B:
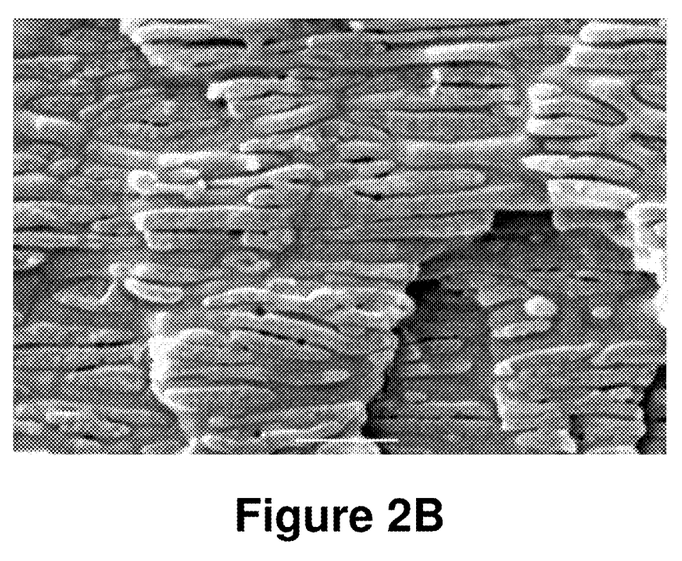
FIG. 2B shows a SEM image of the film of FIG. 2A, as seen in the CD direction.

Similarly, in films with a blend of 70% PPC and 30% CAB, one can observe a similar morphological structure in MD direction to the 30% of PPC blend films. These films exhibit a more amorphous dispersed phase than the films containing 30% PPC blend (FIG. 2A). The same films when examined in CD direction showed a fine "brick and mortar" type structure, with ribbon-like CAB phase dispersed in a matrix of PPC soft polymer (FIG. 2B). As used herein "ribbon-like" or "string-noodle-like" refers to a form in which the morphology of the occlusion is flattened, planar, and has a greatly elongated major dimension greater than its relative minor width, when formed into a film sheet.

The various occlusions behave as microscopic filaments that extend throughout the material matrix of the film. The fine microstructure, it is believed, can help alleviate stresses in the material when it undergoes stretching, bending or other flexing.

The above microstructures supported the observation of poor compatibility of PPC and CAB as shown by the mechanical properties. Therefore, compatibilization of the two polymers is critical for achieving improved mechanical properties.

Microstructures of CAB/PPC Compatibilized by a PHB Compatibilizer

In comparison, the structural feature of a film made from the tertiary blend is a fraction of corresponding features in a precursor binary blend. We have observed that an introduction of the compatbilizer can reduce the dimensions of the structures by at least 7-8%. More typically, the dimensions of the structural morphology is refined and reduced in size between about 10% or 12% to about 75% or 80% of those seen in corresponding binary blend films. More typically the reduction in size may range between about 15% or 17% to about 45% or 55%; or in some embodiments, the size can be reduced by about 20% or 25% to about 30% or 40%. In other words, the morphological features in some embodiments are about 1/10, to about 1/4, 1/3 or 1/2 the size of a corresponding feature in a film of the binary blend system.

For instance, when 5% of PHB is melt blended with CAB/PPC (70/30), the SEM image of the resultant films in MD direction showed a similar but significantly refined layered structure as compared to the unchanged CAB/PPC (70/30) binary blend. For the films with the compatibilizer, the dispersion size of PPC in CAB matrix significantly decreased in the CAB matrix, in contrast to those films without PHB. The SEM image is presented in FIG. 3A.

Figure 4A:
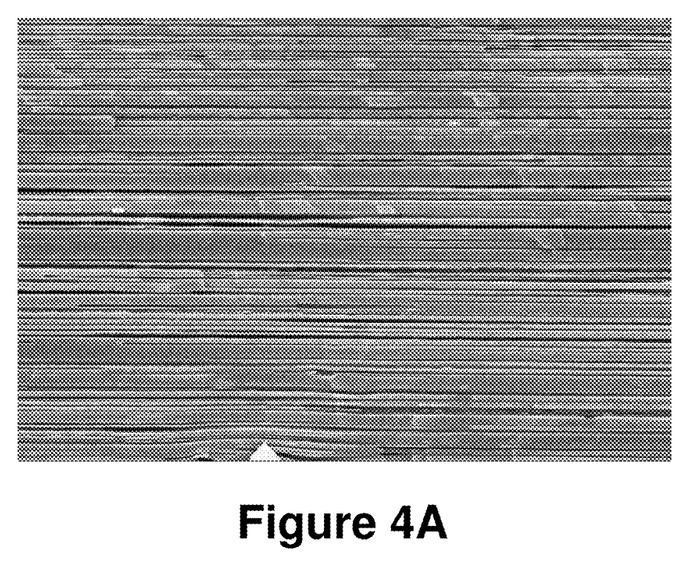
FIG. 4A shows a SEM image of an extruded film material, formed from a tertiary blend of a thermoplastic cellulose derivative (30%), a carbon dioxide polymer (70 wt. %), and an aliphatic polyester (5 wt. %), according to the present invention, as seen along the MD orientation.
Figure 4B:
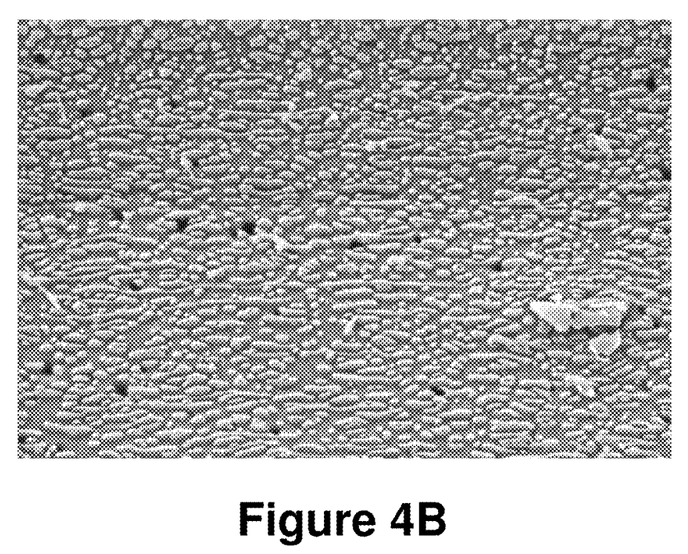
FIG. 4B shows a SEM image of the film of FIG. 4A, as seen in the CD orientation.

Tertiary-blend films composed of CAB and PPC (30/70) with the addition of about 5% to about 20% PHB showed morphology structure similar with that of CAB/PPC/PHB (70/30/5) displaying laminated type structure in MD and island-in-the-sea type of morphology in CD as displayed in FIGS. 4A and 4B.

Figure 3A:
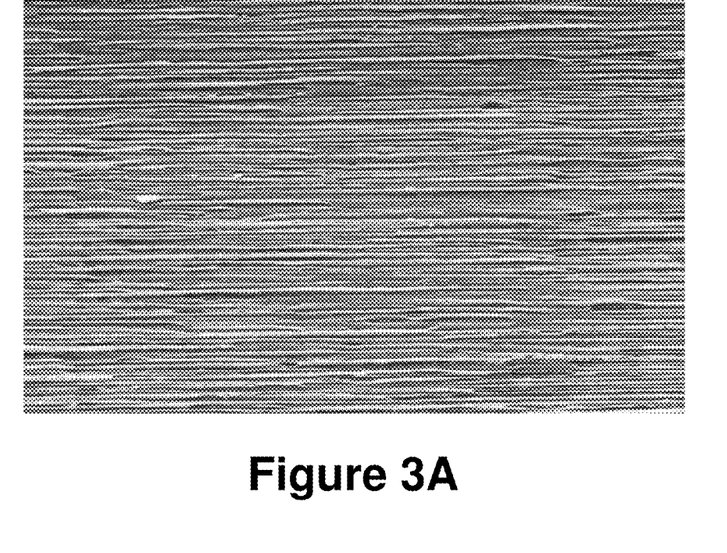
FIG. 3A shows a SEM image of an extruded film material, formed from a tertiary blend of a thermoplastic cellulose derivative (70%), a carbon dioxide polymer (30 wt. %), and an aliphatic polyester (5 wt. %), according to the present invention, as seen along the MD orientation.
Figure 3B:
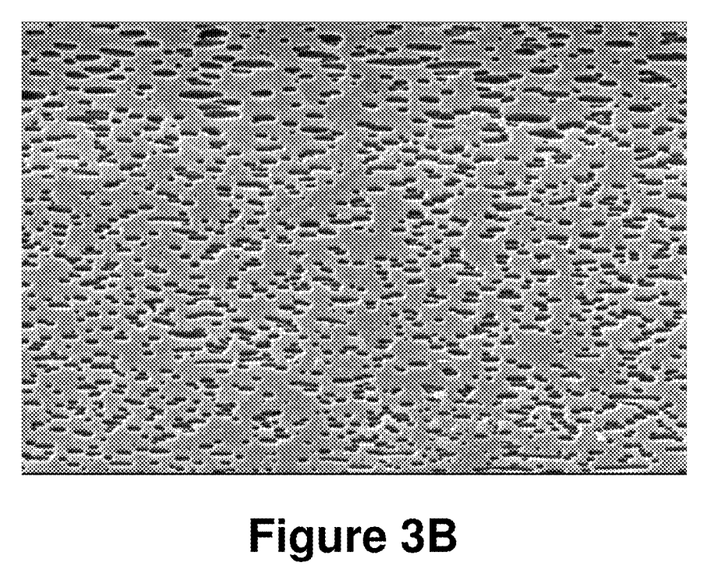
FIG. 3B shows a SEM image of the film of FIG. 3A, as seen in the CD orientation.

In the CD direction, the blend films having the compatibilizer showed an overall "islands-in-a-sea" type of morphology, where the PPC component forms nano-sized "islands" in a "sea" of the CAB matrix, such as shown in FIG. 3B. Overall, the SEM shows that a blend that has been compatibilized will have a nano-dispersed fiber of PPC with a cross section dimension range from about <100 nm to up to about 1 µm. This is an unexpected effect of PHB on the original base or precursor binary blend of CAB/PPC.

Typically in conventional films with a binary blend of CAB/PHB, one observed a heterogeneous morphology with poor dispersion of the minority component or phase in the majority component or phase. This is corroborated by the decrease of peak stress and elongation for the blend films of CAB and PPC. This poor compatibility between these two polymers was structurally modified and improved by the addition of small amount of PHB during melt blending of CAB and PPC polymers. Morphology for blend films of CAB/PPC with the 5% PHB showed the better dispersion of PPC in CAB matrix than that of CAB/PPC without PHB. This microstructure displaying relatively good dispersion of PPC in CAB matrix results in the improvement of ductility over CAB/PPC binary-blend films.

In an un-extruded precursor of the film material, the minor phase occlusions may appear as micro-spherical globules throughout the major phase, which are then flattened and stretched into ribbon-like structures in the film.

Section III—Empirical Examples

The present invention will be further described in detail by the following examples.

Materials

We obtained a carbon dioxide-based polymer: QPAC40®, polypropylene carbonate (PPC) from EMPOWER materials (New Castle, Del., US) and used it as received.

The thermoplastic cellulose derivative, cellulose acetate butyrate (CAB), (grade: Tenite butyrate 485-10, plasticizer: 10% of bis(2-ethylhexyl) adipate, composition: 37 wt. % of butyrate, 13.5 wt % of acetate, DS (degree of substitution): 2.4-2.8), were purchased from Eastman Chemical, Inc. (Minneapolis, Minn.), and used for creating the following examples.

Polyhydroxy butyrate (PHB), Biomer P226, was purchased from Biomer Ltd. (Germany). PHB is an isotactic, linear, thermoplastic aliphatic homopolyester made from of 3-hydroxy butyric acid. PHB is free from even traces of catalyst. PHB is water-insoluble and is highly crystalline (60 to 70%), providing excellent resistance to solvents.

Polyhydroxybutyrate-valerate (PHBV), Enmat® Y100P was purchased from Tianan Biologic Material Co. Ltd. PHBV is a bio-polyester produced via bacterial fermentation of plant starches.

As described herein, the major components (PPC and CAB) in the tertiary blended films are present in a ratio of 70:30 or 30:70 respectively, with a residual of the compatibilizer (PHB or PHBV) in about 5%-17% of the total composition.

Example 1

Films according to the present invention were made on a Thermo Prism™ USALAB 16 twin screw extruder (Thermo Electron Corp., Stone, England), the melt blending and film extrusion were made in the same process; i.e., a direct extrusion and cast film extrusion process. The extruder had 11 zones, numbered consecutively 1-10 from the feed hopper to the die. CAB at 100% was initially added to a feeder that fed the material into feed throat of the extruder. The first barrel received the CAB at a rate of 1.2 lbs/hr. The temperature profile of zones 1 through 10 of the extruder was 175-195° C. for each zone (exact temperatures are listed in Table 4). The die temperature was 180° C. The screw speed was set at 15 rpm and the torque during extrusion process was about 80% to about 85%. Film casting was conducted directly by attaching a 4" film die on the extruder. The film from the 4" die was cooled on a chill roll of a film take-up device. The extrusion process and film casting were done successfully. The CAB film that was obtained appeared clear and had no irregular or un-melted particles and/or other impurities.

Examples 2-6

The melt blending and film casting of PPC and CAB were conducted in the manner described above as in Example 1. The temperature profile of zones and operating conditions are listed in Table 4. All polymers were dry blended and fed to extruder. Film casting was conducted directly by attaching a 4" film die on the extruder. The extrusion process and film casting were done successfully for all compounded resins.

Example 7

A film of 100% PPC was made in the in the manner described above as in Example 1. A first barrel received the PPC at a rate of 1 lbs/hrs. The temperature profile of zone 1 to zone 10 of the extruder was from about 150° C. to about 175° C. for each zone. The die temperature was 175° C. The screw speed was set at 15 rpm and the torque during extrusion process was around 28%. The extrusion process and film casting were done successfully.

Examples 8-10

The tertiary melt blending and film casting of PPC, CAB, and PHB were conducted in the manner described above as in Example 1. The temperature profile of zones and operating conditions are listed in Table 5. About 5 wt. % of PHB was dry blended with PPC and CAB, then fed into the extruder. Film casting was conducted directly by attaching a 4" film die on the extruder. The extrusion process and film casting were done successfully for all compounded resins.

Examples 11-16

The tertiary melt blending and film casting of PPC and CAB and PHBV were conducted in the manner described above in Example 1. The temperature profile of zones and operating conditions are listed in Table 6. 5, 13, 17 wt % of PHBV were dry blended with PPC and CAB, then fed to extruder respectively. Film casting was conducted directly by attaching a 4" film die on the extruder. The extrusion process and film casting were done successfully for all compounded resins.

The present invention has been described in general and in detail in the foregoing examples, which are given for purposes of illustration, and should not to be construed as limiting the scope of this invention, which is defined by the following claims and all equivalents thereto.

TABLE 1

Tensile Properties of Blending Films composed of PPC and CAB

| Experiment No. | Polymer Polymer Ratio (wt.) | | Film Mechanical Properties | | | | | | | | | |
|---|---|---|---|---|---|---|---|---|---|---|---|---|
| | | | Film Thickness (mil.) | | Peak Stress (Mpa) | | Elongation at Break (%) | | Modulus (Mpa) | | Energy at Break (J/cm$^3$) | |
| | CAB | PPC | MD | CD | MD | CD | MD | CD | MD | CD | MD | CD |
| Exp. 1 | 100 | 0 | 1.9 | 1.8 | 83 | 33 | 13 | 38 | 1800 | 1100 | 8 | 10 |
| Exp. 2 | 90 | 10 | 2.5 | 2.4 | 69 | 42 | 19 | 45 | 1700 | 1300 | 10 | 15 |
| Exp. 3 | 70 | 30 | 2.4 | 2.2 | 63 | 44 | 26 | 27 | 1600 | 1400 | 12 | 9 |
| Exp. 4 | 50 | 50 | 1.9 | 1.8 | 68 | 41 | 11 | 37 | 1800 | 1300 | 6 | 12 |
| Exp. 5 | 30 | 70 | 1.9 | 1.9 | 49 | 35 | 20 | 38 | 1700 | 1300 | 8 | 9 |
| Exp. 6 | 10 | 90 | 1.8 | 1.3 | 46 | 33 | 25 | 3.3 | 1500 | 1200 | 9 | 1 |
| Exp. 7 | 0 | 100 | 1.4 | 1.3 | 34 | 32 | 170 | 14 | 1200 | 1200 | 35 | 2 |

TABLE 2

Tensile Property of Blending Films composed of PPC and CAB with 5 wt % of PHB

| Experiment No. | Polymer Polymer Ratio (wt.) | | Film Mechanical Properties | | | | | | | | | |
|---|---|---|---|---|---|---|---|---|---|---|---|---|
| | | | Film Thickness (mil.) | | Peak Stress (Mpa) | | Elongation at Break (%) | | Modulus (Mpa) | | Energy at Break (J/cm3) | |
| | CAB | PPC | MD | CD | MD | CD | MD | CD | MD | CD | MD | CD |
| Exp. 8 | 90 | 10 | 2.1 | 2.1 | 63 | 38 | 50 | 65 | 1277 | 1045 | 23 | 21 |
| Exp. 9 | 70 | 30 | 1.7 | 1.6 | 60 | 35 | 48 | 60 | 1379 | 1066 | 22 | 17 |
| Exp. 10 | 30 | 70 | 1.9 | 1.4 | 46 | 28 | 86 | 183 | 1108 | 875 | 30 | 33 |

TABLE 3

Tensile Property of Blending Films composed of PPC and CAB with PHBV

| Experiment No. | Polymer Ratio (wt %) CAB | Polymer Ratio (wt %) PPC | PHBV addition (wt %) | Film Thickness (mil.) MD | Film Thickness (mil.) CD | Peak Stress (Mpa) MD | Peak Stress (Mpa) CD | Elongation at Break (%) MD | Elongation at Break (%) CD | Modulus (Mpa) MD | Modulus (Mpa) CD | Energy at Break (J/cm³) MD | Energy at Break (J/cm³) CD |
|---|---|---|---|---|---|---|---|---|---|---|---|---|---|
| Exp. 11 | 70 | 30 | 5  | 2.1 | 2.3 | 53 | 37 | 67  | 100 | 1300 | 1200 | 27 | 30 |
| Exp. 12 | 70 | 30 | 13 | 2.4 | 2.1 | 55 | 35 | 55  | 73  | 1200 | 1100 | 23 | 21 |
| Exp. 13 | 70 | 30 | 17 | 2.1 | 1.9 | 58 | 34 | 70  | 69  | 1300 | 1000 | 30 | 20 |
| Exp. 14 | 30 | 70 | 5  | 2.3 | 2.6 | 52 | 35 | 80  | 140 | 1400 | 1200 | 32 | 32 |
| Exp. 15 | 30 | 70 | 13 | 2   | 1.9 | 49 | 32 | 89  | 120 | 1100 | 1100 | 32 | 29 |
| Exp. 16 | 30 | 70 | 17 | 2   | 1.9 | 50 | 26 | 110 | 250 | 1100 | 940  | 40 | 54 |

TABLE 4

Processing Conditions of Extruding CAB/PPC Blend Films

| Experiment No. | Polymer ratio (wt) CAB | Polymer ratio (wt) PPC | Z1 | Z2 | Z3 | Z4 | Z5 | Z6 | Z7 | Z8 | Z9 | Z10 | Feed lbs/hrs | Ext. rpm | Torque % | Pressure bar |
|---|---|---|---|---|---|---|---|---|---|---|---|---|---|---|---|---|
| Exp. 1 | 100 | 0   | 175 | 175 | 180 | 180 | 185 | 185 | 195 | 195 | 195 | 195 | 1.2 | 15 | 80~85 | 28 |
| Exp. 2 | 90  | 10  | 180 | 180 | 180 | 180 | 185 | 185 | 185 | 190 | 190 | 185 | 1.2 | 12 | 50~55 | 23 |
| Exp. 3 | 70  | 30  | 170 | 170 | 170 | 175 | 175 | 175 | 180 | 180 | 180 | 180 | 0.8 | 10 | 52~58 | 22 |
| Exp. 4 | 50  | 50  | 170 | 170 | 170 | 175 | 175 | 175 | 180 | 180 | 180 | 180 | 1   | 12 | 48~53 | 22 |
| Exp. 5 | 30  | 70  | 165 | 165 | 165 | 170 | 170 | 170 | 175 | 175 | 175 | 175 | 1   | 13 | 46~50 | 18 |
| Exp. 6 | 10  | 90  | 165 | 165 | 165 | 170 | 170 | 170 | 175 | 175 | 175 | 175 | 1   | 15 | 55 | 17 |
| Exp. 7 | 0   | 100 | 150 | 165 | 165 | 165 | 170 | 170 | 170 | 175 | 175 | 175 | 1   | 15 | 28 | 12 |

TABLE 5

Processing Conditions of Extruding CAB/PPC Blend Films with the addition of 5 wt. % of PHB

| Experiment No. | Polymer ratio (wt) CAB | Polymer ratio (wt) PPC | Z1 | Z2 | Z3 | Z4 | Z5 | Z6 | Z7 | Z8 | Z9 | Z10 | Feed lbs/hrs | Ext. rpm | Torque % | Pressure bar |
|---|---|---|---|---|---|---|---|---|---|---|---|---|---|---|---|---|
| Exp. 8  | 90 | 10 | 170 | 170 | 170 | 175 | 175 | 175 | 180 | 180 | 185 | 185 | 1.3 | 20 | 47~52 | 18 |
| Exp. 9  | 70 | 30 | 170 | 170 | 170 | 175 | 175 | 175 | 180 | 180 | 180 | 180 | 1.3 | 20 | 38~42 | 15 |
| Exp. 10 | 30 | 70 | 165 | 165 | 165 | 170 | 170 | 170 | 175 | 175 | 175 | 175 | 1.3 | 20 | 40~43 | 16 |

TABLE 6

Processing Conditions of Extruding CAB/PPC Blend Films with the addition of 5, 13, 17 wt % of PHBV

| Experiment No. | Polymer ratio (wt %) CAB | Polymer ratio (wt %) PPC | PHBV addition (wt %) | Z1 | Z2 | Z3 | Z4 | Z5 | Z6 | Z7 | Z8 | Z9 | Z10 | Feed lbs/hrs | Ext. rpm | Torque % | Pressure bar |
|---|---|---|---|---|---|---|---|---|---|---|---|---|---|---|---|---|---|
| Exp. 11 | 70 | 30 | 5  | 170 | 170 | 170 | 175 | 175 | 175 | 180 | 180 | 180 | 185 | 1 | 20 | 44~48 | 20 |
| Exp. 12 | 70 | 30 | 13 | 170 | 170 | 170 | 175 | 175 | 175 | 180 | 180 | 180 | 185 | 1 | 20 | 41~45 | 19 |
| Exp. 13 | 70 | 30 | 17 | 170 | 170 | 170 | 175 | 175 | 175 | 180 | 180 | 180 | 185 | 1 | 20 | 38~42 | 18 |
| Exp. 14 | 30 | 70 | 5  | 165 | 165 | 165 | 170 | 170 | 170 | 176 | 176 | 176 | 175 | 1 | 20 | 38~40 | 16 |
| Exp. 15 | 30 | 70 | 13 | 165 | 165 | 165 | 170 | 170 | 170 | 175 | 175 | 175 | 175 | 1 | 20 | 36~38 | 16 |
| Exp. 16 | 30 | 70 | 17 | 165 | 165 | 165 | 170 | 170 | 170 | 175 | 175 | 175 | 175 | 1 | 20 | 38~40 | 18 |

We claim:

1. A flexible thermoplastic film comprising:
a tertiary blend of 1) about 1 wt. % to about 95 wt. % of a polyalkylene carbonate and 2) about 95 wt. % to about 1 wt. % of a thermoplastic cellulose derivative, respectively forming a either a major or minor component of said film, and 3) 5 wt. % to 17 wt. % of a polyhydroxyalkanoate (PHA) compatibilizer; wherein said film exhibits nanostructural features that are at least 1/3 to 1/10 of the size of corresponding structural morphology in a film formed from a binary blend of a precursor thermoplastic material of said polyalkylene carbonate and said thermoplastic cellulose derivative, absent said polyhydroxyalkanoate (PHA) compatibilizer, wherein said nanostructure features have a nano-dispersed fiber morphology and form one of two phases composed of either said polyalkylene carbonate or said thermoplastic cellulose derivative, whichever one of the two is present as a minority species in said majority component, wherein said film exhibits an elongation percent-at-break value that is increased by at least 150% to about 500% of a film formed from a binary blend of a polyalkylene carbonate and a thermoplastic cellulose derivative absent said polyhydroxyalkanoate (PHA) compatibilizer.

2. The film according to claim 1, wherein said nanostructural features are evenly distributed like islands-in-a-sea throughout a material body of said film.

3. The film according to claim 1, wherein said film exhibits an islands-in-a-sea type morphology of nanostructural features of polyalkylene carbonate dispersed in a matrix of thermoplastic cellulose derivative material, when said polyalkylene carbonate is a minority species; wherein said nanostructural features have an average length dimension from about 1/8 to about 3/4 of a micrometer.

4. The film according to claim 1, wherein said film exhibits an elongation percent-at-break value increase of about 150% to about 700% relative to a film formed from said binary blend in a machine-direction orientation.

5. The film according to claim 1, wherein said film exhibits an elongation percent-at-break value increase of about 200% to about 500% relative to a film formed from said binary blend along a cross-direction orientation.

6. The film according to claim 1, wherein said tertiary blend film exhibits an energy-at-break improvement of about 200% to about 800% relative to said binary blend film.

7. An absorbent article or health care product comprising the film of claim 1.

8. The absorbent article according to claim 7, wherein said film is part of an inner baffle or an outer cover.

9. The absorbent article according to claim 7, wherein said article is a personal hygiene product, a feminine care product, a diaper, a training pant, or an adult incontinence product.

10. A packaging film comprising the film according to claim 1.

11. The film according to claim 1, wherein said film exhibits an islands-in-a-sea type morphology of nanostructural features of thermoplastic cellulose derivative dispersed in a matrix of polyalkylene carbonate material, when said thermoplastic cellulose derivative is a minority species; wherein said nanostructural features have an average length dimension from about 1/8 to about 3/4 of a micrometer.

12. The film according to claim 1, wherein said film exhibits a modulus in the machine direction ranging from 1100 megapascals to 1400 megapascals and exhibits a modulus in the cross direction ranging from 875 megapascals to 1200 megapascals.

\* \* \* \* \*